(12) United States Patent
Feiner et al.

(10) Patent No.: US 7,059,320 B2
(45) Date of Patent: Jun. 13, 2006

(54) INHALATION THERAPY APPARATUS

(75) Inventors: Franz Feiner, München (DE); Markus Borgschulte, München (DE)

(73) Assignee: Pari GmbH Spezialstein fur Effektive Inhalation, Starnberg (DE)

( * ) Notice: Subject to any disclaimer, the term of this patent is extended or adjusted under 35 U.S.C. 154(b) by 0 days.

(21) Appl. No.: 10/492,788

(22) PCT Filed: Oct. 16, 2002

(86) PCT No.: PCT/EP02/11582

§ 371 (c)(1),
(2), (4) Date: Sep. 20, 2004

(87) PCT Pub. No.: WO03/035152

PCT Pub. Date: May 1, 2003

(65) Prior Publication Data

US 2005/0034719 A1    Feb. 17, 2005

(30) Foreign Application Priority Data

Oct. 18, 2001  (EP) ................................. 01124295

(51) Int. Cl.
*A61M 11/00*    (2006.01)

(52) U.S. Cl. .............................. 128/200.16; 128/203.12
(58) Field of Classification Search ........... 128/200.14, 128/200.16, 200.31, 203.12
See application file for complete search history.

(56) References Cited

U.S. PATENT DOCUMENTS 6,131,570 A    10/2000   Schuster et al.

FOREIGN PATENT DOCUMENTS

| EP | 0 919 252 | 6/1999 |
|----|-----------|--------|
| WO | 01/00263  | 1/2001 |

*Primary Examiner*—Aaron J. Lewis
(74) *Attorney, Agent, or Firm*—Merchant & Gould P.C.

(57) ABSTRACT

The invention relates to an inhalation therapy apparatus comprising an aerosol generating device (1, 6, 7) for atomizing a liquid (3), a connecting device (8, 9) for supplying a control signal, and a control device (10) from which a control signal of the connecting device can be supplied to the aerosol generating device whereby causing the aerosol generating device to atomize the liquid. To this end, an output signal, which is elicited by the breathing of the patient on the connecting device (8, 9) of the aerosol generating device (1, 6, 7) is supplied to the control device (10) for controlling the inhalation therapy apparatus.

15 Claims, 2 Drawing Sheets

INHALATION THERAPY APPARATUS

FIELD OF THE DISCLOSURE

The invention relates to inhalation therapy apparatuses having an aerosol generator, in particular with an oscillatable membrane for nebulising a liquid or powder.

BACKGROUND

The control of inhalation therapy apparatuses occurs in many cases under consideration of the respiration of the patient so as to only generate the aerosol during inhalation or to provide the aerosol for inhalation. In this manner, an improved application of the medicament contained in the aerosol is achieved on the one hand and a reduction in medicament losses is achieved on the other. It is necessary for this manner of controlling inhalation apparatuses to reliably detect the respiration of the patient during inhalation therapy. Respiration sensors are used for this purpose in the known inhalation nebulisers, which detect the pressure fluctuations caused by the respiration of the patient and convert them into an output signal which is supplied to a control means of the inhalation nebuliser, is evaluated therein and is converted into suitable control processes.

SUMMARY OF THE INVENTION

The invention shows a way in which control of an inhalation therapy apparatus can occur subject to the respiration of the patient, without a separate respiration sensor being used. The expenditure during production of the inhalation nebuliser is thereby reduced and the breakdown susceptibility thereof is decreased.

This is achieved according to the invention by means of an inhalation therapy apparatus comprising an oscillatable membrane for nebulising a liquid, an oscillation generating device which has at least one connecting means for supplying an activation signal and by means of which the membrane is caused to oscillate when the activation signal is supplied such that a liquid disposed on one side of the membrane is nebulised through the membrane and is present on the other side of the membrane as an aerosol, and comprising a control means from which an activation signal can be supplied to the at least one connecting means of the oscillation generating device such that the oscillation generating device causes the membrane to oscillate, whereby according to the invention, an output signal generated by the respiration of the patient at the at least one connecting means of the oscillation generating device is supplied to the control means for controlling the inhalation therapy apparatus.

The invention is based on the quite surprising realisation that in membrane nebulisers, the electromechanical transducer unit used to cause oscillation, generally a piezoelectric component, provides a respiration-dependent output signal which can be used to control the inhalation therapy apparatus, namely regardless of whether the membrane nebuliser is activated or not.

Thus, the design according to the invention achieves the advantage that a respiration sensor of the aforementioned type is no longer necessary. The reason for this is that a separate respiration sensor is not needed in an inhalation therapy apparatus according to the invention since an output signal of the aerosol generator resulting from the respiration of the patient is used to control activation of the aerosol generator.

The solution according to the invention is basically suitable for all inhalation therapy apparatuses using an aerosol generator that generates a respiration-dependent output signal which can be picked up, processed, in particular separately from the activation signal, and evaluated for control. The applicability of the invention is thus not restricted to membrane nebulisers although nebulisers of this type are especially advantageous.

The invention can thus be characterised, even in abstract, as an inhalation therapy apparatus comprising an aerosol generating device for nebulising a liquid or powder which has a connecting means for supplying an activation signal, and comprising a control means from which an activation signal can be supplied to the connecting means of the aerosol generating device such that the aerosol generating device nebulises the liquid, in which an output signal caused by the respiration of the patient at the connecting means of the aerosol generating device is supplied to the control means for controlling the inhalation therapy apparatus.

It is also advantageous in the solution according to the invention that additional electrodes or other additional signal pick-ups or diversions are not necessary. The reason for this is that the diversion of the respiration signal preferably occurs via the existing electrodes or connecting lines; it is not necessary to interfere with the design of the electromechanical transducer unit or the design of the inhalation nebuliser.

The fact that the construction of the inhalation nebuliser and the aerosol generator thereof does not have to be interfered with also means that existing inhalation therapy apparatuses can be retrofitted. The reason for this is that in order to equip an existing inhalation therapy apparatus with the possible control functions according to the invention, it is sufficient to exchange the control unit thereof, which is generally realised as a separate device, for a control unit in which evaluation of the respiration signal according to the invention occurs.

It is advantageous with regard to the retrofitting of existing devices as described above, but also fundamentally, if processing of the output signal occurs in the same structural unit or even inside the same electrical unit in which the control means is also realised since additional connecting lines for diverting the respiration signal can be avoided in this manner. This is particularly important in inhalation therapy apparatuses in which the control and other components, for example the power supply, are accommodated in a housing which is separate from the nebuliser. When using the invention, it is sufficient for the connection between the nebuliser and the control unit to provide the line connections required for transmitting the activation signal to the aerosol generator. The pick-up of the output signal caused by the respiration of the patient can also occur via these connecting lines.

BRIEF DESCRIPTION OF THE DRAWINGS

The invention will be explained in more detail below by means of an embodiment and referring to the figures:

FIG. 1 shows a schematic representation of an inhalation therapy apparatus according to the invention; and FIG. 2 shows a block diagram of the processing unit of the inhalation therapy apparatus according to the invention shown in FIG. 1.

DETAILED DESCRIPTION

Figure 1:
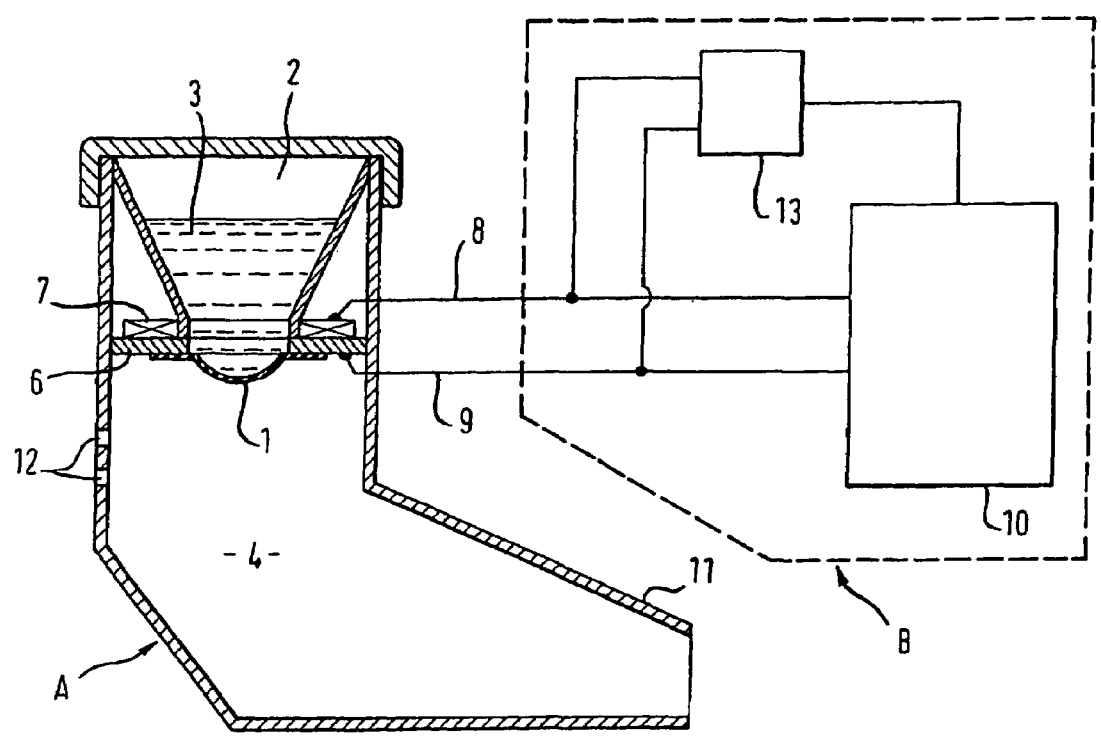

Shown in FIG. 1 is an embodiment of an inhalation therapy apparatus according to the invention, in which in a nebuliser unit A, a liquid 3 stored in a liquid reservoir 2 is nebulised by means of a membrane 1 into a nebulisation cavity 4. Nebulisation occurs when the membrane 1 is caused to oscillate. For this purpose, the membrane 1 is attached to a support unit 6 which supports the membrane 1 and to which an electromechanical transducer unit 7, for example a piezo element, is also attached. The membrane 1, the support unit 6 and the electromechanical transducer unit 7 are configured in a rotationally symmetrical manner in the embodiment described herein and together form an oscillatable structure. An activation signal of a control means 10 can be supplied to the electromechanical transducer unit 7 via connecting lines 8 and 9, said control means 10 being accommodated in a separate control unit B in the embodiment described herein.

When the activation signal is supplied, the oscillatable structure 1, 6, 7 is caused to oscillate and the liquid 3 is nebulised through the membrane 1.

A patient can inhale the aerosol provided in the nebulisation cavity 4 at the mouthpiece 11 of the nebuliser. So that there is a sufficient supply of air, one or more air holes 12 are provided in the housing of the nebuliser, through which ambient air can enter into the cavity 4 during inhalation and out of which the air inhaled by the patient can exit from the cavity 4 during exhalation. In comparison with the environment outside of the cavity 4, pressure fluctuations occur in the cavity 4 during inhalation and exhalation. During inhalation the pressure in the nebuliser chamber 4 sinks below the ambient pressure and during exhalation it rises above the ambient pressure. Although pressure equalisation occurs due to the air holes 12, it was, however, found by the tests leading to the invention described herein that the pressure fluctuations are generally sufficient to act upon the membrane 1 such that a usable respiration-dependent output signal is emitted by the electromechanical transducer unit 7. The extent of the pressure fluctuations and thus the intensity of the effect of respiration of the patient upon the membrane 1 can be influenced by the design of the air holes 12 and preferably also by correspondingly designed valve elements at the air holes 12.

In the shown embodiment, an output signal caused by the respiration of the patient is available at the two connecting lines 8 and 9 which can also be used to supply the activation signal to the oscillatable structure 1, 6, 7. Since excitation of the membrane 1 is caused by a signal whose frequency is much higher than the respiration frequency of a person, the output signal, which results from the pressure fluctuations in the nebulisation cavity 4 caused by the respiration of the patient, can be picked-up at the activation connection 8, 9 of the oscillatable structure 1, 6, 7. According to the invention, this respiration signal is supplied to the control means 10 and is taken into account therein when activating the inhalation therapy apparatus.

As shown in the embodiment described herein, a suitable processing unit 13 is preferably provided, which is configured as a separate unit, for example as a filter/amplifier circuit, and which processes the output signal, which is influenced by the respiration of the patient, at the connections of the oscillatable structure 1, 6, 7, i.e. the aerosol generator, into a control signal which follows the respiration cycle of the patient. This signal is used by the control means 10 such that the activation of the oscillatable structure 1, 6, 7 and thus nebulisation of the liquid 3 through the membrane 1 only occurs in the desired sections of the respiration cycle, for example only during inhalation.

In this manner, a simple on/off switching operation can be realised according to the invention, i.e. nebulisation starts when inhalation begins and ends once inhalation is complete. However, it was established during the tests based on the invention that the respiration signal of the oscillatable structure 1, 6, 7, which is usable according to the invention, allows for considerably more accurate information regarding the respiratory cycle of the patient, namely even if the activation signal is also supplied to the oscillatable structure 1, 6, 7 via the connecting lines 8 and 9. In other words, the two signals, namely the activation signal of the control means 10, by means of which the oscillatable structure 1, 6, 7 is caused to oscillate, and the output signal of the oscillatable structure 1, 6, 7, caused by the respiration of the patient, superpose one another in an almost distortion-free manner. This is quite surprising since the output signal at the connecting means 8, 9 of the oscillatable structure 1, 6, 7, which is caused by pressure fluctuations, is much smaller than the activation signal which is fed from the control means 10 to the oscillatable structure 1, 6, 7 via the connecting lines 8 and 9. Therefore, when using the invention, optical or acoustical indications can be given to the patient to optimise respiratory flow, or aerosol generation can be automatically shut-off if too high respiratory flows are detected which are unfavourable for a safe intrapulmonary aerosol deposition.

In order to ensure a reliable separation of the respiration signal and the activation signal, the control means 10 is preferably configured such that no low-frequency signal components, in particular no dc components, are used to activate the oscillatable structure 1, 6, 7 for nebulising the liquid 3. It is also achieved by means of this design that the output signal caused by the respiration of the patient can be separated from the activation signal with comparatively little effort and thus in an inexpensive manner.

The embodiment described in more detail above shows how the use according to the invention of the respiration signal occurs in an inhalation therapy apparatus having a membrane nebuliser. The description of the embodiment, however, also makes it clear that the invention can be applied to all inhalation therapy apparatuses in which an aerosol generating device is supplied with an activation signal in order to generate an aerosol, and in which the respiration of the patient acts upon the aerosol generating device such that an output signal is available which can be supplied to the control means to activate the aerosol generating device.

The invention can be primarily used in such inhalation therapy apparatuses in which an electromechanical transducer unit is provided, which causes an oscillatable structure that effects generation of the aerosol to begin to oscillate. Pressure fluctuations caused by the respiration of the patient regularly act upon the oscillatable structure and lead to movements of the oscillatable structure which correspond to the pressure fluctuations. These movements resulting from the pressure fluctuations produce an output signal which is generated as a result of the movement of the electromechanical transducer unit.

Inhalation therapy apparatuses in which the electromechanical transducer unit is configured in the form of a piezoelectric element are particularly suitable for the use of the invention.

Figure 2:
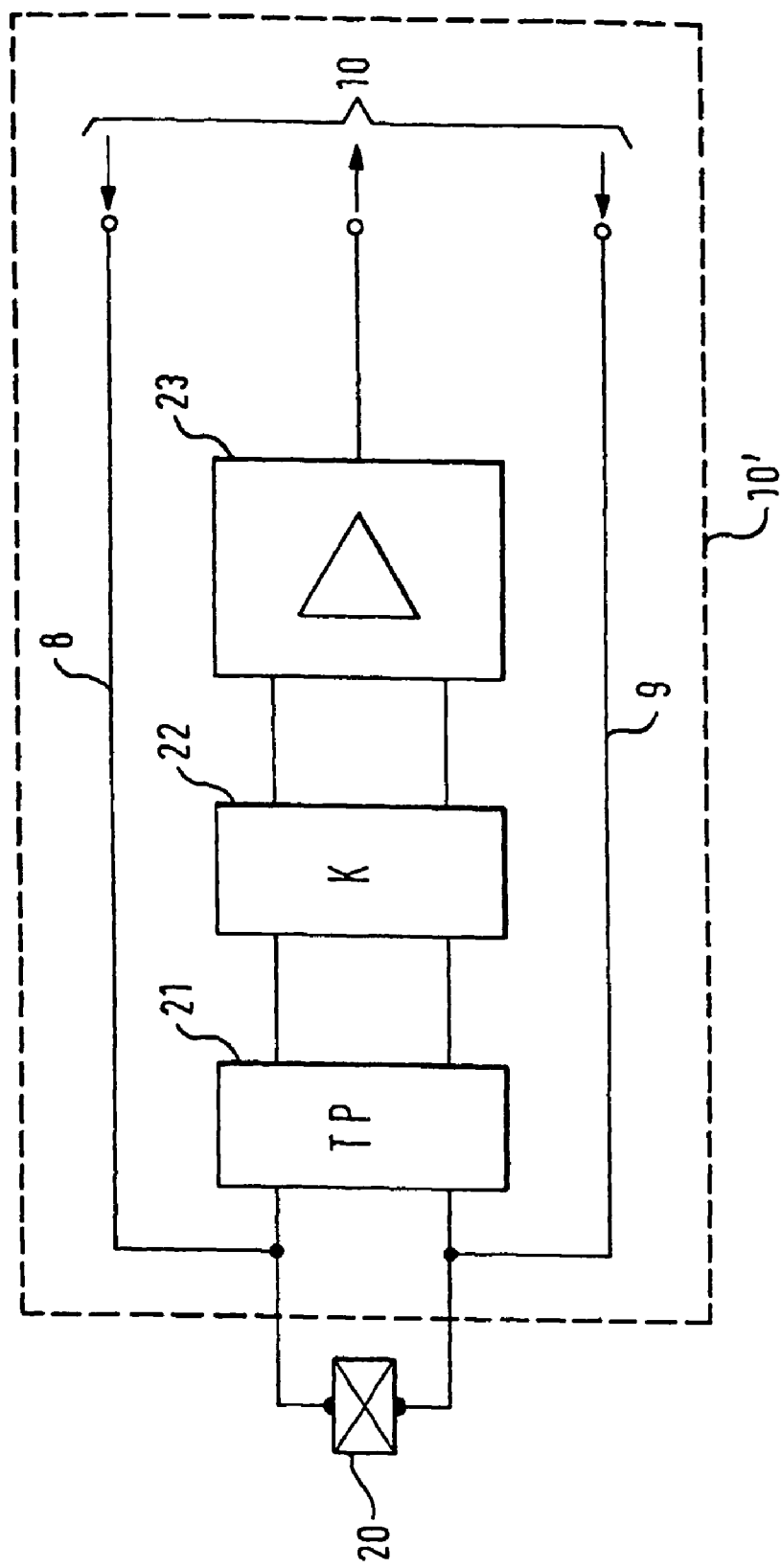

As shown in FIG. 2, the processing unit 13 of the embodiment described herein comprises the sub-units described below. To simplify the representation in FIG. 2, the oscillatable structure, consisting of the membrane 1, the support element 6 and the piezo element 7, has been replaced in FIG. 2 by a schematic representation of an electromechanical piezo transducer 20. The respiration-influenced output signal of the piezo transducer 20, picked-up at the connecting means, is supplied in the processing unit 13 to a low-pass unit 21 which initially filters out the high frequency components of the picked-up signal and thus, in particular, the components of the picked-up signal caused by the activation signal. The output signal of the low-pass filter 21 is supplied to a coupling unit 22, formed, for example, from capacitors having a suitable capacity. The output signal of the coupling unit 22 is supplied to an amplifier unit 23 which converts the supplied signal into a suitable output signal for the control unit 10.

As indicated by arrows in FIG. 2, the respiration signal processed by the processing unit 13 is supplied to the control means 10, from which the activation signal for the piezo transducer 20 is supplied via the connecting lines 8 and 9. The dashed line in FIG. 2 indicates that the control means 10 and the processing means 13 can be arranged in a common housing or even in a single circuit arrangement/circuit.

The invention claimed is:

1. Inhalation therapy apparatus comprising:
   a. an oscillatable membrane (1) for nebulising a liquid (3),
   b. an oscillation generating device (6, 7) operably connected to said membrane (1), said oscillation generating device (6, 7) having at least one connecting means (8, 9) for supplying an activation signal and by means of which said membrane (1) is caused to oscillate when the activation signal is supplied such that a liquid disposed on one side of said membrane is nebulised through the membrane and is present on the other side of said membrane as an aerosol, and
   c. a control means (10), from which the activation signal can be supplied to the at least one connecting means (8, 9) of the oscillation generating device (6, 7) so that said oscillation generating device (6, 7) causes the membrane (1) to oscillate, wherein the oscillation generating device (6, 7) provides an output signal caused by the respiration of a patient at the at least one connecting means (8, 9) of the oscillation generating device (6, 7) is supplied to the control means (10) for controlling the inhalation therapy apparatus.

2. Inhalation therapy apparatus according to claim 1, wherein the oscillation generating device (6, 7) comprises an electromechanical transducer unit (7), in particular a piezoelectric element.

3. Inhalation therapy apparatus according to claim 2, wherein the oscillation generating device (6, 7) comprises a support unit (6) to which the electromechanical transducer unit (7) and the membrane (1) are attached.

4. Inhalation therapy apparatus according to claim 1, further comprising a processing unit (13), via which the output signal at the at least one connecting means (8, 9) of the oscillation generating device (6, 7) is supplied to the control means (10), and which provides a respiration signal which follows the respiration process of the patient.

5. Inhalation therapy apparatus according to claim 4, wherein the processing unit (13) comprises a low-pass unit (21), a coupling unit (22) and an amplifier unit (23).

6. Inhalation therapy apparatus according to claim 4 wherein the processing unit (13) is integrated in the control means (10).

7. Inhalation therapy apparatus according to claim 1, wherein an energy supply means for the inhalation apparatus is integrated in the control means (10).

8. Inhalation therapy apparatus according to claim 1, wherein the control means (10) is integrated in an energy supply means for the inhalation therapy apparatus.

9. Inhalation therapy apparatus comprising:
   a. an aerosol generating device (1, 6, 7) for nebulising a liquid (3) or powder, having a connecting means (8, 9) for supplying an activation signal, and
   b. a control means (10) from which the activation signal can be supplied to the connecting means (8, 9) of the aerosol generating device (1, 6, 7) so that said aerosol generating device nebulises the liquid or powder, wherein the aerosol generating device (1, 6, 7) provides an output signal caused by the respiration of a patient at the connecting means (8, 9) of the aerosol generating device (1, 6, 7) is supplied to the control means (10) for controlling the inhalation therapy apparatus.

10. Inhalation therapy apparatus according to claim 9, wherein the aerosol generating device comprises an oscillatable structure upon which the respiration of the patient acts such tat a respiration-dependent output signal is produced.

11. Inhalation therapy apparatus according to claim 9 wherein the aerosol generating device comprises an electromechanical transducer unit (7), preferably a piezoelectric element.

12. Inhalation therapy apparatus according to claim 9, wherein a processing unit (13) is provided, via which the output signal of the aerosol generating device (1, 6, 7) is supplied to the control means (10), and which provides a respiration signal which follows the respiration process of the patient.

13. Inhalation therapy apparatus according to claim 12, wherein the processing unit (13) comprises a low-pass unit (21), a coupling unit (22) and an amplifier unit (23).

14. Inhalation therapy apparatus according to claim 12, wherein the processing unit (13) is integrated in the control means (10).

15. Inhalation therapy apparatus according to claim 12, wherein the control means (10) is integrated in an energy supply means for the inhalation therapy apparatus.

* * * * *

UNITED STATES PATENT AND TRADEMARK OFFICE
CERTIFICATE OF CORRECTION

PATENT NO. : 7,059,320 B2  Page 1 of 1
APPLICATION NO. : 10/492788
DATED : June 13, 2006
INVENTOR(S) : Feiner et al.

It is certified that error appears in the above-identified patent and that said Letters Patent is hereby corrected as shown below:

Title page, item (56) References Cited, U.S. Patent Documents: Insert

| | | |
|---|---|---|
| --3,812,854 | 05/1974 | Michaels et al. |
| 4,001,650 | 01/1977 | Romain |
| 4,106,503 | 08/1978 | Rosenthal et al. |
| 4,319,155 | 03/1982 | Nakai et al. |
| 4,790,479 | 12/1988 | Matsumoto et al. |
| 5,363,842 | 11/1994 | Mishelevich et al. |
| 6,402,046 | 06/2002 | Loser |
| 6,546,927 | 04/2003 | Litherland et al.-- |

Title page, item (56) References Cited, Foreign Patent Documents: Insert
--GB    2164569 A   03/1986--

Col. 1, line 3: "FIELD OF TILE DISCLOSURE" should read --FIELD OF THE DISCLOSURE--

Col. 6, line 33, claim 10: "acts such tat a" should read --acts such that a--

Signed and Sealed this

First Day of May, 2007

JON W. DUDAS
*Director of the United States Patent and Trademark Office*